United States Patent
Johnson, II et al.

(10) Patent No.: US 9,873,641 B2
(45) Date of Patent: Jan. 23, 2018

(54) REACTOR MULTI-PASS GRIDS FOR IMPROVED CATALYST HYDRODYNAMICS

(71) Applicant: UOP LLC, Des Plaines, IL (US)

(72) Inventors: Richard A. Johnson, II, Algonquin, IL (US); Paolo Palmas, Des Plaines, IL (US); John J. Senetar, Naperville, IL (US); Daniel A. Kauff, Arlington Heights, IL (US); Michael Stine, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 209 days.

(21) Appl. No.: 14/225,465

(22) Filed: Mar. 26, 2014

(65) Prior Publication Data
US 2014/0296603 A1  Oct. 2, 2014

Related U.S. Application Data

(60) Provisional application No. 61/806,493, filed on Mar. 29, 2013.

(51) Int. Cl.
| | |
|---|---|
| *C07C 1/22* | (2006.01) |
| *C07C 1/20* | (2006.01) |
| *B01J 8/12* | (2006.01) |
| *B01J 8/00* | (2006.01) |

(52) U.S. Cl.
CPC .................. *C07C 1/20* (2013.01); *B01J 8/008* (2013.01); *B01J 8/12* (2013.01); *B01J 2208/0084* (2013.01); *B01J 2208/00663* (2013.01); *B01J 2208/00938* (2013.01); *C07C 2529/85* (2013.01)

(58) Field of Classification Search
CPC .. C07C 1/20; C07C 11/02; B01J 2208/00663; B01J 2208/0084; B01J 2208/00938; B01J 8/008; B01J 8/12
USPC ................................ 585/638, 639, 640, 641
See application file for complete search history.

(56) References Cited

U.S. PATENT DOCUMENTS

| | | | |
|---|---|---|---|
| 3,957,689 A | 5/1976 | Ostermaier | |
| 4,071,573 A * | 1/1978 | Owen | B01J 8/1836 |
| | | | 423/DIG. 13 |
| 4,987,110 A | 1/1991 | Scherzer | |
| 5,008,088 A * | 4/1991 | Fremuth | C10G 3/49 |
| | | | 422/187 |
| 5,352,645 A | 10/1994 | Schwartz | |
| 7,829,030 B2 * | 11/2010 | Beech, Jr. | B01J 8/0055 |
| | | | 422/139 |

OTHER PUBLICATIONS

U.S. Appl. No. 14/225,464 filed Mar. 26, 2014, Johnson.

* cited by examiner

*Primary Examiner* — Sharon Pregler

(57) ABSTRACT

A process and device for the flow of catalyst in a reactor is presented. The device includes a series of grids within a reactor vessel, where each grid includes small openings for the passage of gas and some catalyst particles, and larger openings for the more continuous passage of catalyst. The grids span horizontally across the vessel, and are spaced vertically apart to provide for the flow of catalyst down through the reactor.

17 Claims, 1 Drawing Sheet

US 9,873,641 B2

REACTOR MULTI-PASS GRIDS FOR IMPROVED CATALYST HYDRODYNAMICS

CROSS REFERENCE TO RELATED APPLICATION

This application claims the benefit of U.S. Provisional Application No. 61/806,493 filed on Mar. 29, 2013.

FIELD OF THE INVENTION

The present invention relates to processes and apparatuses utilizing reactor internals for the distribution of catalysts in a reactor. Specifically, this invention relates to designs for the internals of an MTO reactor to provide for a better distribution of catalyst and contacting of the catalyst with the reactants.

BACKGROUND OF THE INVENTION

Ethylene and propylene, or light olefins, are important for the production of commercially important plastics, namely polyethylene and polypropylene. Other important polymer precursors include vinyl chloride, ethylbenzene, ethylene oxide and other compounds, which are derived from the light olefins. The production of light olefins is primarily produced through the cracking of heavier hydrocarbons from hydrocarbon feedstocks derived from petroleum.

A light olefin plant is a combination of reactors and gas recovery systems. The reactors include cracking units for generating a stream having light olefins and fractionation units for separating the light olefins from the other hydrocarbon components in the product streams from the reactors.

The increasing demand for light olefins has led to the search for other sources as the cost of petroleum has increased. Among the new sources include oxygenates that can be derived from biomass, and other sources. Common oxygenates include alcohols and in particular methanol. In particular, natural gas comprising primarily methane can be converted to methanol, and the methanol can be converted to light olefins. The oxygenates are converted through a reaction process to generate a product stream comprising light olefins.

One conversion process is generally referred to as methanol to olefins (MTO) process, and the process involves a catalytic reaction and is carried out in a catalytic reactor to generate a product stream of light olefins. The catalyst for the conversion of oxygenates to olefins include solid catalyst such as zeolites. Zeolites used in the MTO process are described in numbers patents. A process for preparing zeolites is described in U.S. Pat. No. 3,957,689. A process for making an improved attrition resistant catalyst is described in U.S. Pat. No. 4,987,110. A process for producing hardened microspheres is described in U.S. Pat. No. 5,352,645. Numerous other patents describe the making of better catalyst for improved reactions, and for improved hardness of the catalyst particles.

Catalysts having improved attrition resistance is important because the reactor environment is a severe physical environment. The MTO reactor is generally a fluidized bed and the catalyst particles are subject to constant contact and rubbing against other catalyst particles and with physical equipment where the catalyst particles are transferred through, or stirred within.

Improving the system for the production of light olefins can increase the catalyst life and improve the process to make the production more economical.

SUMMARY OF THE INVENTION

The present invention is a process and device for improving the contact and yields of light olefins generated in an oxygenate conversion process. The apparatus comprises a plurality of grids disposed within the reactor, where the grids are comprised of small openings and at least one large opening. The large openings facilitate the flow of catalyst while minimizing the catalyst holdup, and direct the catalyst to flow at least partially across the grids as the catalyst flows down the reactor.

The process comprises flowing a oxygenate rich stream over the catalyst in a generally counter-current flow, with the catalyst flowing down the reactor vessel and the gas flowing up the vessel. The process contacts the oxygenate rich stream with the catalyst at reaction conditions, while flowing the catalyst in a generally serpentine path down the reactor vessel. The movement of the catalyst minimizes the formation of dense catalyst regions, and minimizes catalyst segregation in the process.

Other objects, advantages and applications of the present invention will become apparent to those skilled in the art from the following detailed description and drawings.

DETAILED DESCRIPTION OF THE INVENTION

There are many reactor processes that utilize fluidized catalyst beds. The catalyst beds are fluidized for providing good contact between the catalyst and reactants. A methanol to olefins (MTO) reactor utilizes a deep catalyst bed. Along with improving the catalyst, improving the conditions within the reactor are also important. The catalyst bed in the MTO is a deep fluidized catalyst bed and flows downward through the reactor. Deep catalyst bed can develop regions where the catalyst does not flow well, and where gas can be maldistributed within the reactor. To improve the movement of catalyst within the reactor and the flow and contact with the gas reactants, vertical plates, or grids, were placed within the reactors. The grids contributed to improving the uniformity of catalyst within the reactor bed. This leads to improve product yields. The grids extend horizontally across the reactor bed and are positioned at multiple elevations within the catalyst bed.

Figure 1:
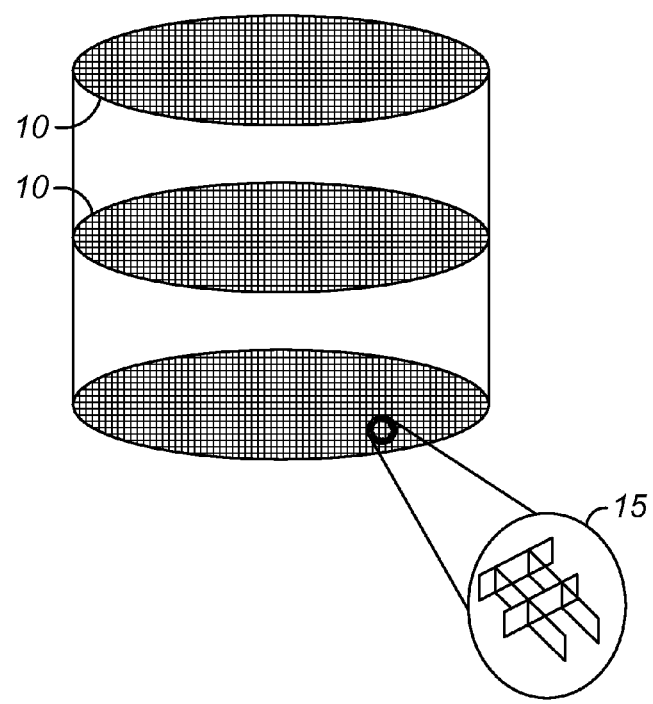
FIG. 1 shows a grid structure for the full coverage of the cross-section of an MTO reactor.

The grids are designed to achieve a sufficient open area, or cross-sectional area, so as to not affect the process, while still maintaining adequate strength to support the grids. If the cross sectional area of the grids is too high, the flow of catalyst can be restricted and lead to poorer reactor performance through localized catalyst segregation. A grid structure, as shown in FIG. 1, shows the internals for an MTO reactor. FIG. 1 shows a stack of three grids 10 that are placed within a reactor vessel. The catalyst enters the top of the reactor and flows down through the reactor and through each of the grids 10. The grids 10 are made of welded strips of metal to form a lattice structure having openings sufficient for the catalyst to flow downward and the gas to flow upward in the reactor. The metal strips are typically 2 to 5 mm thick with a width between 10 and 20 mm, but can have a greater thickness or width, depending on the size of the reactor and the strength needed for the grid within the reactor. The lattice structure formed will have substantially rectangular, or square, openings having a side measurement from 10 to 50 mm. The grids are designed to have a large open area, and preferably the open area is greater than 65% of the cross sectional area, and more preferably greater than 75%.

A problem with a uniform grid arises from the counter-current flow patterns of catalyst and gas. The grids facilitate the flow of catalyst in a uniform direction by limiting the upward and downward motion of the catalyst. However, the flow of gas and the spectrum of particle sizes of the catalyst creates some segregation of the catalyst and creates regions of increased catalyst densities and regions of lower catalyst densities. This is due to smaller particles of catalyst being held up and having greater difficulty flowing across the grids.

The present invention is directed to improving the flow of catalyst through the direction of large scale flow of catalyst through the reactor and to limit or prevent the creation of localized high velocity areas and localized non-uniform catalyst density regions. The process for this invention concerns contacting an oxygenate feedstream with the catalyst, while flowing the catalyst down through the reactor and flowing the feedstream up through the reactor.

FIG. 1 shows the layout for three grids used in a normal reactor, wherein the grids 10 span the entire cross-section of a reactor. FIG. 1, also shows an inset 15, showing an enlargement of a section of a grid. The grid is open and allows for the flow of catalyst through the grid, while also allowing for the flow of fluid in an opposing direction, or upward, through the grid.

Figure 2:
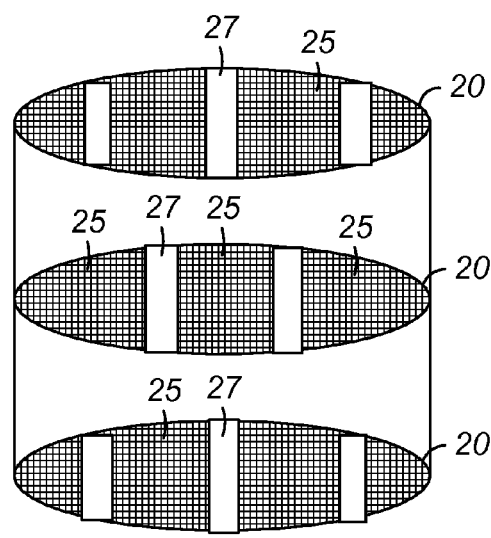
FIG. 2 shows one grid structure for allowing the catalyst to flow more smoothly down the reactor.

The present invention includes a reactor for contacting a solid catalyst with fluid reactants. The reactor comprises a vessel, where the vessel has an inlet for the catalyst, an outlet for the catalyst, an inlet for the fluid, and an outlet for the fluid. In one embodiment, the fluid is a gas, where the solid flows downward, and the gas flows upward. The interior of a reactor is shown in FIG. 2, where there are a plurality of grids 20 disposed within the reactor vessel. The grids 20 extend horizontally across the vessel, and there is a vertical spacing between each pair of grids 20. The grids 20 include a plurality of small openings 25 of sufficient size to allow gas through the openings 25, and of sufficient size to allow the catalyst particles to flow through the openings 25. The grids 20 also include at least one large opening 27 in the grid. The large openings 27 are sufficiently large to allow for the catalyst particles to flow freely.

The large openings 27 in each grid comprise an open space of between 15% and 35% of the total cross-sectional area. Preferably, the large openings comprise an open space between between 15% and 25% of the total cross-sectional area.

The grids 20 are disposed within the reactor in a vertical stacking, with vertical spacing between each pair of grids 20. With respect to neighboring grids, each grid has a horizontal orientation, and the large openings are offset in the horizontal direction relative to the large openings of neighboring grids 20. The large openings 27 are substantially rectangular, having a width and a length, with the length greater than the width. The large openings 27 have a width between 5 and 50 mm. In a preferred embodiment, the large openings 27 are substantially rectangular or trapezoidal in shape, and the length of the large openings 27 span the grid from one edge to an opposing edge.

In one embodiment, the reactor grids 20 comprise a plate with small openings distributed over the plate. Each grid 20 spans the horizontal cross-section of the reactor vessel, and has at least on end that is spaced at least 10 mm from one side of the vessel. This spacing between the grid and the vessel wall provides a large opening, as defined in the present invention. In an alternate embodiment, the reactor can have grids having spacing between the wall and the grid, wherein neighboring grids have the spacing between the wall and the grid on opposite sides of the vessel. The openings in each grid 20 provide a total open area to allow catalyst and fluid to flow, between 50% and 90% of the total cross-sectional area of a grid. In a preferred embodiment, the total open space, or sum of the spaces of the openings, provides a total open area that is between 70% and 85% of the total cross-sectional area.

Preferably, the reactor includes at least three grids 20 stacked within the vessel in a vertical arrangement. Each grid has at least two large openings that are substantially rectangular, or trapezoidal, in shape, and where each large opening in the grid spans the width of the grid. The large openings of neighboring grids are also displaced, in a horizontal direction relative to the large openings of a neighboring grid.

In one embodiment, the reactor grids comprise a structure for controlling the flow of catalyst particles through a reactor vessel, wherein the grid has a cross-sectional area and is disposed in a substantially perpendicular orientation relative to the movement of catalyst. The grid 20 comprises a plurality of small openings wherein each small opening 25 has a small dimension between 5 mm and 25 mm. The grids further include at least one large opening, wherein each large opening has a small dimension of at least 75 mm. The large openings in each grid comprises between 15% and 35% of the total cross-sectional area, and preferably between 20% and 30% of the total cross-sectional area.

In one embodiment, a grid comprises two large openings, and wherein each of the two large openings comprises between 5% and 20% of the total cross-sectional area, with the sum of the two openings comprising at least 15% of the total cross-sectional area. In a preferred embodiment each large opening comprises between 5% and 15% of the total cross-sectional area.

In another embodiment, the large opening is disposed on one side of the grid between the edge of the grid and the vessel wall, and comprises between 15% and 25% of the total cross-sectional area.

In one embodiment, the grid comprises a series of intersecting metal strips oriented perpendicular to the plane of the grid. The intersecting metal strips form a lattice structure comprising small openings and at least one large opening.

The addition of multi-pass grids will prevent the formation of increased catalyst density areas from forming, and improve the overall flow of catalyst through the reactor vessel. This provides for improved contact between the catalyst and fluid, and improves reactor yields. The grids prevent localized high velocity areas with respect to the vertical movement of the catalyst. The catalyst is not allowed to freely flow down from the top of the reactor to the catalyst outlet. The catalyst flows downward, but also is directed to flow across, or partially across, the reactor. This provides for catalyst mixing, as well as breaking up of void spaces and prevents the formation of high density catalyst volumes. The improved flow patterns due to the grid design reduces catalyst segregation.

The smaller openings provide for fluid, or gas, flow upward, but allows for some catalyst flow through the small openings. With just an array of small openings, the catalyst can segregate and gas flow will preferentially find a path of least resistance, thereby creating segregated catalyst regions.

The large openings direct the catalyst and facilitate the flow of catalyst through the reactor and minimize the segregation of catalyst.

Another aspect of the invention is a process for the production of olefins from oxygenates. The process includes passing a catalyst to a reactor, as described above. The catalyst flows down through the reactor, and a feedstream comprising oxygenates is passed to the reactor through a reactor inlet disposed near the bottom of the reactor vessel. The feedstream flows upward and over the catalyst, reacting and generating an outlet process stream comprising olefins. The grids provide for the flow of catalyst across at least part of the reactor vessel as the catalyst flows downward through the reactor.

The feedstream comprises a fluid having oxygenates. The oxygenates can include alcohols, ethers, aldehydes, ketones, carboxylic acids, and mixtures thereof. In a preferred embodiment of the process, the oxygenates include alcohols and ethers. It is more preferred that the feed comprises methanol, or dimethyl ether, or a combination of both.

The present invention uses any appropriate catalyst for the conversion of oxygenates to olefins. A preferred catalyst is a zeolite or a non-zeolitic molecular sieve. A preferred catalyst comprises a silicoaluminophosphate (SAPO).

The process is operated at reaction conditions to convert the oxygenates to olefins over the catalyst. The reaction conditions include a temperature in the range from 200° C. and 700° C., with a preferred range from 300° C. to 600° C. The pressures in the reactor for the conversion are between 100 kPa to 10 MPa, with a preferred range from 170 kPa to 2 MPa.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the production of olefins from oxygenates comprising:
    passing a catalyst downward through a reactor for contacting a solid catalyst with fluid reactants;
    passing fluid reactants comprising oxygenates upward through the reactor in a counter current mode with respect to the catalyst;
        contacting the catalyst in the reactor with a plurality of grids disposed within the reactor and extend horizontally across the reactor, and with a vertical spacing between pairs of grids,
        directing, at each grid, at least a portion of the catalyst to flow at least partially across the reactor through contact with a plurality of small openings in each grid of sufficient size to allow gas through and the catalyst particles through, wherein the small openings each have a first open area;
        directing, at each grid, at least a portion of the catalyst to flow freely downward by passing at least a portion of the catalyst though at least one large opening in each grid wherein the large opening has a second open area greater than the first open area; and
    reacting the fluid reactants comprising oxygenates through the contact of the fluid reactants with the catalyst at reaction conditions effective to convert the oxygenates into olefins and generating an effluent comprising olefins.

2. The process of claim 1 wherein the directing of the catalyst to flow flows freely downward through the at least one large opening occurs over between 15% and 35% of the cross-sectional area of each grid.

3. The process of claim 1 wherein the directing of the catalyst to flow flows freely downward through the at least one large opening occurs over between 15% and 25% of the cross-sectional area of each grid.

4. The process of claim 1 wherein the fluid reactants comprising oxygenates includes oxygenates selected from the group consisting of alcohols, ethers, aldehydes, ketones, carboxylic acids, and mixtures thereof.

5. The process of claim 1 wherein the directing of the catalyst to flow flows freely downward through the large openings in the grids occurs across a substantially rectangular area having a width between 5 and 50 mm and which spans across the grid.

6. The process of claim 1 wherein the directing of the catalyst to flow flows freely downward through the large openings in the grids occurs in a space between the reactor wall and the grid.

7. The process of claim 1 wherein the catalyst comprises a molecular sieve comprising silicoaluminophosphates.

8. The process of claim 1 wherein the catalyst particle flow is directed by at least three grids stacked within a vessel in a vertical arrangement, and where each grid has at least two large opening that are substantially rectangular, and where the openings span the width of the grid, and wherein the large openings are displaced in a horizontal direction relative to the large openings of a neighboring grid.

9. A process for converting oxygenates to olefins, comprising:
    passing a catalyst downward through a reactor, wherein the reactor includes a plurality of reactor grids
        controlling the flow of catalyst particles through the reactor by contacting the flow of catalyst particles with a structure having a cross-sectional area and disposed in a substantially perpendicular orientation relative to the movement of catalyst
        wherein the flow of catalyst particles is restricted by a plurality of small openings in the structure wherein each small opening has a small dimension between 5 and 25 mm; and
        wherein the flow of catalyst particles unrestricted by at least one large opening in the structure wherein the large opening has a minimum small dimension of at least 75 mm and wherein the large opening comprises between 15% and 35% of the cross-sectional area of the structure; and
    contacting a fluid stream comprising oxygenates over the catalyst at reaction conditions in the reactor to generate a process stream comprising olefins.

10. The process of claim 9 wherein in each reactor grid the large opening comprises between 20% and 30% of the cross-sectional area.

11. The process of claim 9 wherein in each reactor grid the at least one large opening comprises two openings, and wherein each of the two large openings comprise between 5% and 20% of the cross-sectional area of the structure.

12. The process of claim 9 wherein the grid comprises one large opening on one side of the grid and comprising between 15% and 25% of the cross sectional area of the grid, and where the remainder of the grid is comprised of small openings.

13. The process of claim 9 wherein the catalyst comprises a zeolite or non-zeolitic molecular sieve.

14. The process of claim 13 wherein the catalyst comprises a silicoaluminophosphate (SAPO).

15. The process of claim 9 wherein the reaction conditions include a temperature between 200° C. and 700° C.

16. The process of claim 9 wherein the fluid stream comprising oxygenates are selected from the group consisting of alcohols, ethers and mixtures thereof.

17. The process of claim 9 wherein the reaction conditions include a pressure between 100 kPa and 2000 kPa.

* * * * *